US006572594B2

(12) United States Patent
Satterfield et al.

(10) Patent No.: US 6,572,594 B2
(45) Date of Patent: Jun. 3, 2003

(54) SKIN TREATMENT USING NEUROMUSCULAR STIMULATION AND A TREATMENT GAS CONTAINING MEDICINE

(75) Inventors: Elaine T. Satterfield, Commerce, GA (US); John Ray, Gainesville, GA (US); Timothy J. Cagle, Alpharetta, GA (US)

(73) Assignee: R.S. Medical Equipment LLC, Gainesville, GA (US)

( * ) Notice: Subject to any disclaimer, the term of this patent is extended or adjusted under 35 U.S.C. 154(b) by 26 days.

(21) Appl. No.: 09/772,214

(22) Filed: Jan. 29, 2001

(65) Prior Publication Data

US 2001/0020145 A1 Sep. 6, 2001

Related U.S. Application Data

(63) Continuation-in-part of application No. 09/376,916, filed on Aug. 18, 1999, now Pat. No. 6,179,804.

(51) Int. Cl.$^7$ ............................................. A61M 35/00
(52) U.S. Cl. ......................... 604/290; 604/23; 604/20; 607/3; 607/50
(58) Field of Search ........................... 604/20, 23, 289, 604/290; 607/1, 3, 50

(56) References Cited

U.S. PATENT DOCUMENTS

| 2,418,473 | A | 4/1947 | Lambertsen et al. |
|---|---|---|---|
| 2,998,817 | A | 9/1961 | Armstrong |
| 3,089,492 | A | 5/1963 | Owens |
| 3,467,081 | A | 9/1969 | Glass |
| 3,610,238 | A | 10/1971 | Rich, Jr. |
| 3,744,491 | A | 7/1973 | Fischer |
| 3,920,006 | A | 11/1975 | Lapidus |
| 4,003,371 | A | 1/1977 | Fischer |
| 4,181,128 | A | 1/1980 | Swartz |
| 4,182,329 | A | 1/1980 | Smit et al. |
| 4,224,941 | A | 9/1980 | Stivala |

(List continued on next page.)

FOREIGN PATENT DOCUMENTS

| SU | 419226 | 8/1974 |
|---|---|---|
| SU | 438417 | 1/1975 |

OTHER PUBLICATIONS

Kung et al., "Enhancement of Wound Healing Using Synthetic Skin, Electric Simulation and Hyperbaric Oxygen Therapy," J. Rehabil. Res. Dev., 28/1 (476), 1991. (See attached citation from database search for date of Pub).*

Joseph McCulloch, PT, PhD, The Wound Care Information Network web page http://www.medicaleduc.com/ultrasnd.htm.

(List continued on next page.)

Primary Examiner—Brian L. Casler
Assistant Examiner—Jeremy Thissell
(74) Attorney, Agent, or Firm—David G. Maire; Beusse Brownlee Bowdoin & Wolter, P.A.

(57) ABSTRACT

A method of treating skin including the application of a treatment gas to a surface of the skin and simultaneous neuro-muscular stimulation of the skin. The increased blood flow resulting from the neuro-muscular stimulation improves the effectiveness of the treatment gas. A medicine may be applied to the skin along with the treatment gas and the temperature of the treatment gas may be controlled to achieve a desired therapy. In one embodiment, a wound is treated by stimulating neuro-muscular activity near the wound while simultaneously applying an antibiotic and oxygen gas to the wound at a first warm temperature and then at a second cool temperature. The treatment gas applicator used to deliver the oxygen to the wound may further be used to provide repeatable measurements of the size of the wound over time. Other beneficial skin effects, such as hair growth and age retardation, may be achieved by applying specific treatment gases and medicines simultaneously with neuro-muscular stimulation.

20 Claims, 6 Drawing Sheets

U.S. PATENT DOCUMENTS

| | | | |
|---|---|---|---|
| 4,236,513 A | | 12/1980 | LoPiana |
| 4,305,390 A | | 12/1981 | Swartz |
| 4,328,799 A | | 5/1982 | LoPiano |
| 4,407,282 A | | 10/1983 | Swartz |
| 4,444,183 A | | 4/1984 | Heckendorn |
| 4,474,571 A | | 10/1984 | Lasley |
| 4,480,638 A | | 11/1984 | Schmid |
| 4,509,513 A | | 4/1985 | Lasley |
| 4,576,173 A | | 3/1986 | Parker et al. |
| 4,592,361 A | | 6/1986 | Parker et al. |
| 4,608,041 A | | 8/1986 | Nielsen |
| 4,685,447 A | | 8/1987 | Iversen et al. |
| 4,772,259 A | | 9/1988 | Fresh et al. |
| 4,778,446 A | | 10/1988 | Jensen |
| 4,801,291 A | | 1/1989 | Loori |
| 4,969,881 A | | 11/1990 | Viesturs |
| 5,029,579 A | | 7/1991 | Trammell |
| 5,135,477 A | | 8/1992 | Untereker et al. |
| 5,154,697 A | | 10/1992 | Loori |
| 5,156,591 A | | 10/1992 | Gross et al. |
| 5,279,544 A | | 1/1994 | Gross et al. |
| 5,338,412 A | | 8/1994 | Burk et al. |
| 5,344,440 A | | 9/1994 | Stephen |
| 5,403,834 A | * | 4/1995 | Malfroy-Camine et al. . 514/185 |
| 5,405,366 A | | 4/1995 | Fox et al. |
| 5,456,700 A | | 10/1995 | Horiguchi |
| 5,478,310 A | | 12/1995 | Dyson-Cantwell et al. |
| 5,607,691 A | * | 3/1997 | Hale et al. .................. 424/449 |
| 5,662,625 A | | 9/1997 | Westwood |
| 5,696,109 A | * | 12/1997 | Malfroy-Camine et al. . 514/184 |
| 5,788,682 A | | 8/1998 | Maget |
| 5,810,795 A | | 9/1998 | Westwood |
| 5,827,880 A | * | 10/1998 | Malfroy-Camine et al. . 514/492 |
| 5,855,570 A | | 1/1999 | Scherson et al. |
| 5,974,344 A | | 10/1999 | Shoemaker, II |
| 6,000,403 A | | 12/1999 | Cantwell |
| 6,094,599 A | | 7/2000 | Bingham et al. |
| 6,115,637 A | | 9/2000 | Lennox et al. |
| 6,458,109 B1 | | 10/2002 | Henley et al. |

OTHER PUBLICATIONS

Ultrasound for cutaneous would heaing web page http://www.jr2.ox.ac.uk/Bandolier/booth/alternat/AT032.html.

Light Therapy for Wound Healing web page http://www.lightmask.com/Polar.htm.

Bioptron Products Healthy through light! web page http://www.bioptron.com/pages/products.htm.

Chronic Wounds Effectively Treated With New ElctroRegenesis Therapy Device web page http://biz.yahoo.com/bw/001214/nv_electro.html.

* cited by examiner

SKIN TREATMENT USING NEUROMUSCULAR STIMULATION AND A TREATMENT GAS CONTAINING MEDICINE

This application is a continuation-in-part of application Ser. No. 09/376,916 filed on Aug. 18, 1999, and issued as U.S. Pat. No. 6,179,804 on Jan. 30, 2001.

FIELD OF THE INVENTION

The present invention relates generally to the field of skin care, and, more particularly, to devices and methods for treating skin with a combination of a treatment gas and simultaneous neuro-muscular electrical stimulation.

BACKGROUND OF THE INVENTION

The use of oxygen to promote healing of wounds, burns, and infections has been documented. Nielsen discloses a device for treatment of wounds by exposure to jets in U.S. Pat. No. 4,608,041. A series of inlet and outlet openings ventilate a space between the device and the wound area. The device is fixed over the area of the wound by means of plaster or tape.

Loori discloses a collapsible topical hyperbaric apparatus in U.S. Pat. No. 5,154,697. A gas inlet tube introduces oxygen to a shell covering the treated area. An adhesive sealing ring on the bottom of the unit secures the device to the affected area in conjunction with a belt.

These and other devices, while providing a chamber to apply oxygen to a wound, are difficult to apply, remove and re-apply. The previous devices are sometimes ineffective in particularly difficult-to-heal wounds.

Neuro-muscular electrical stimulation is the known technique of applying an electrical current to the skin to stimulate the contraction of muscles. One known device for performing neuro-muscular electrical stimulation is the RS-2 Muscle Stimulator provided by RS Medical, Inc. of Vancouver, Wash. Neuro-muscular stimulation is used to stimulate the flow of blood to an area of the skin by repeated contraction and relaxation of nearby muscles.

SUMMARY OF THE INVENTION

It has been found that the simultaneous application of a treatment gas such as oxygen to the skin while simultaneously providing electrical stimulus to the same area of skin promotes beneficial effects such as wound healing, hair growth, pain relief and generally improved health of the skin tissues. The treatment gas may further be used as a carrier for the delivery of various medicines to the skin surface, wherein the improved circulation generated by the neuro-muscular stimulation results in the efficient absorption of the medicine into the body. The method promotes healing of wound areas not responsive to other forms of treatment. Wounds, burns and infections which have been unresponsive to treatment gas application alone are responsive when subjected to both treatment gas and electrical stimulation in adjacent areas.

A method of treating a wound is described herein as including providing a flow of oxygen to the wound while applying an electrical current to the skin proximate the wound. The oxygen may be provided through a treatment gas applicator adhered to or positioned proximate the skin. The electrical current may be provided through at least one electrode attached to the skin proximate the wound.

One embodiment is described wherein a medicine is provided within the flow of a treatment gas to the surface of the skin. An electrical current applied to the skin to cause neuro-muscular contractions will increase the flow of blood in the skin, thereby aiding in the absorption of the medicine into the blood stream through the skin surface. Medicines that may be administered in this manner include antibiotics, pain medication, hair growth compounds, vitamins and other nutrients, etc.

The temperature of the flow of treatment gas to the skin may be controlled as part of a skin treatment regiment to reduce pain and/or to curb infection. In one embodiment for the treatment of a wound, the temperature of the treatment gas is at least 103 degrees Fahrenheit during a first time period and no more than 94 degrees Fahrenheit during a second time period.

A variety of benefits may be obtained by a method of treating skin including the steps of providing a flow of a treatment gas to a skin surface and applying an electrical current to the skin surface during the step of providing a flow of treatment gas. Such benefits may include retarding the aging of skin, reducing wrinkles, stimulating hair growth and improved healing of wounds. The application of electrical current to the skin increases the circulation of blood near the skin surface, thereby facilitating the absorption of the treatment gas components into the skin and blood stream.

A device for delivering a treatment gas to a wound may include a seal gasket adhered to the skin with an age-degradable adhesive. The seal gasket may also be used as a base for the repeated application of a grid pattern for photographically measuring the size of a wound over a plurality of time periods. By disposing the grid pattern very close to the wound, the accuracy of the wound measurements is made less sensitive to changes in the height of the camera used to photograph the grid/wound.

BRIEF DESCRIPTION OF THE DRAWINGS

These and other features, aspects and advantages of the present invention will become better understood with regard to the following description, appended claims and accompanying drawings where:

DESCRIPTION OF THE PREFERRED EMBODIMENTS

Figure 1:
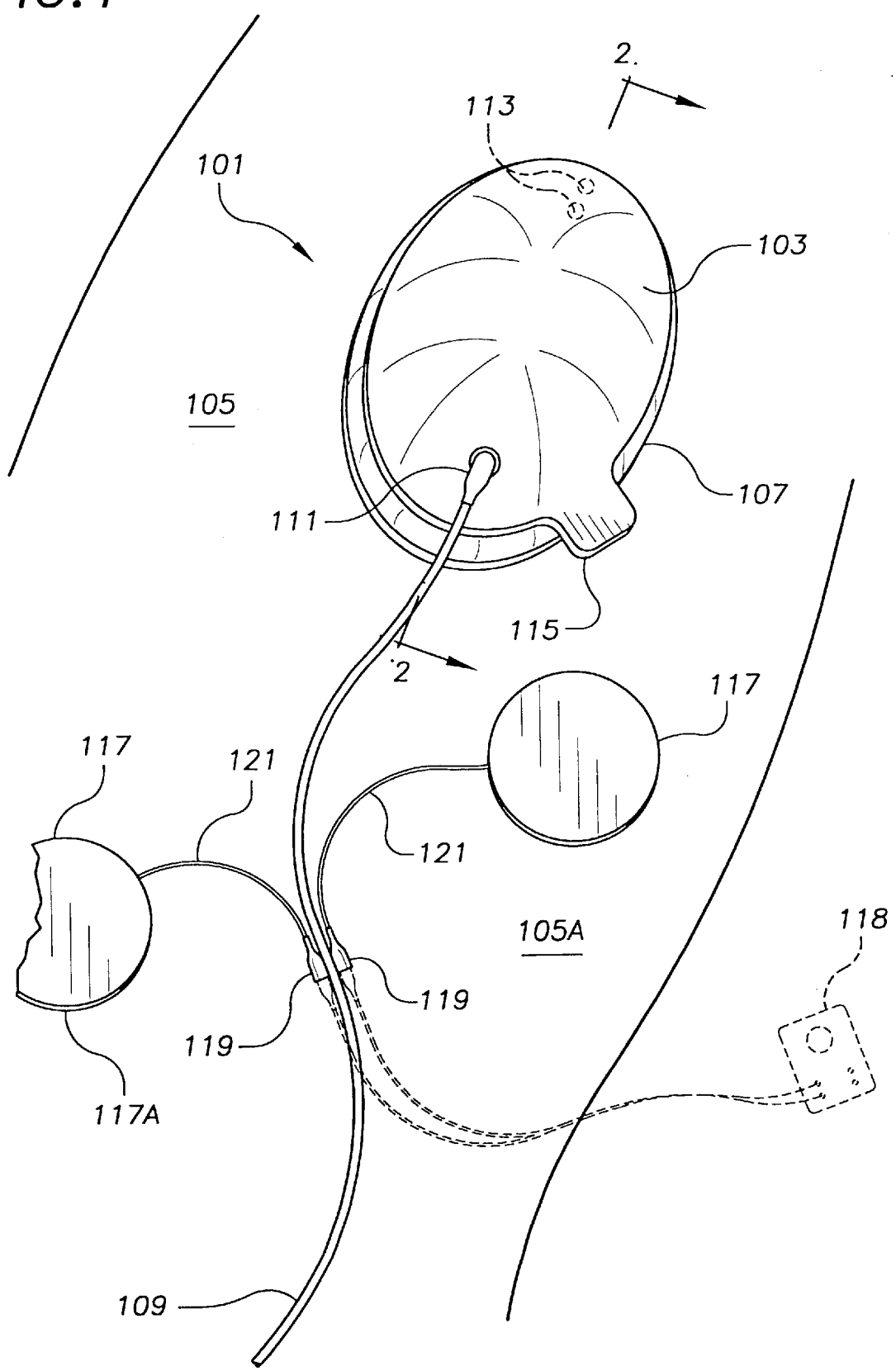
FIG. 1 is a perspective drawing of an embodiment of oxygen application apparatus showing an inflatable dome attached to a skin portion surrounding a wound by a seal gasket, and two stimulation electrodes attached to an oxygen supply hose.
Figure 2:
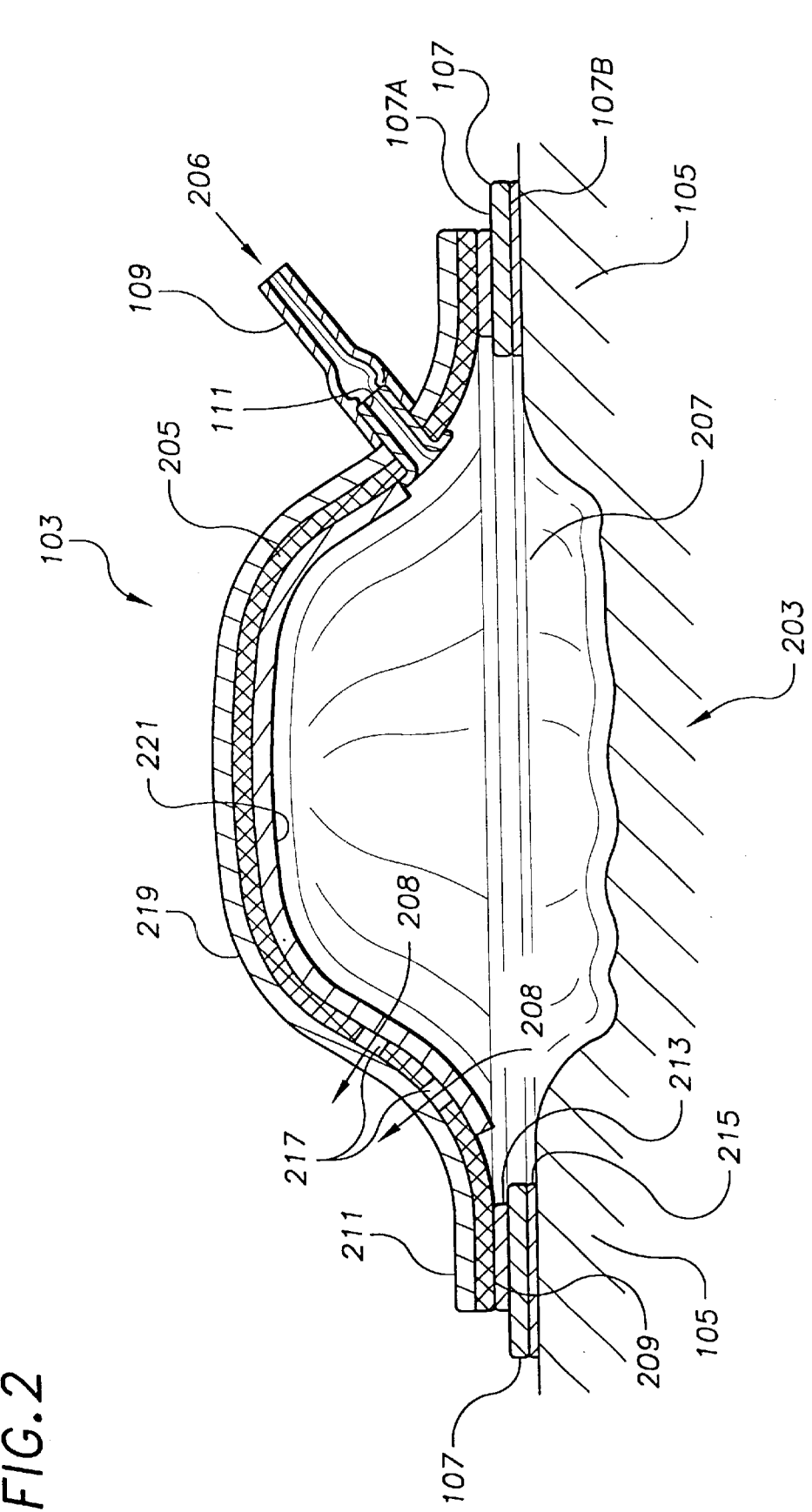
FIG. 2 is a cross section of the inflatable dome and seal gasket taken along lines 2—2 of FIG. 1.

FIG. 1 is a perspective drawing of treatment apparatus 101 covering a wound area (203 of FIG. 2). The apparatus consists of an inflatable dome portion 103 attached to surrounding skin portion 105 by seal gasket 107. Oxygen supply hose 109 supplies oxygen to inflatable dome 103 through fitting or nozzle 111. Gas vents 113 vent gasses inside dome 103 to atmosphere. Tab 115 promotes removal of dome portion 103 from seal gasket 107.

Neuro-muscular stimulation electrodes such as electrode patches 117 provide electrical connections to surrounding skin portion 105A to promote blood supply to the wound area and further promote healing. A power supply 118 supplies electric current to electrode patch 117 through plugs 119 and current carrying conductors or wires 121. Plugs 119 are attached to oxygen supply hose 109 by adhesives, welding, or mechanical connectors. Alternatively, plugs 119 are connected to dome portion 103. A contact adhesive attached to the bottom 117A of electrode patches 117 attaches the patches to surrounding skin portion 105A. The electrodes 117 may be integrated into the seal gasket assembly 107.

FIG. 2 is a cross section drawing of inflatable dome portion 103 taken along lines 2—2 of FIG. 1. Membrane 205 is a flexible gas barrier providing the structure of dome portion 103 when inflated by a gas such as oxygen. In the preferred embodiment, membrane 205 is made of a polymeric sheet or film such as polyolefin film. Other materials include PVC, fluoropolymers, and natural and synthetic rubber sheets and films. In alternative embodiments, membrane 205 is a rigid or semi-rigid material such as plastic, formed in a dome shape. Dome peripheral portion 211 may be the peripheral portion of membrane 205, or it may be a ring-shaped element bonded by adhesives, welding, or fasteners to membrane 205. In the preferred embodiments, peripheral portion 211 is flexible to provide sealing with seal gasket 107 on uneven portions of the body.

Oxygen supply hose 109 provides oxygen flow 206 to dome interior portion 207 through nozzle 111 inserted through an aperture in membrane 205. Nozzle 111 is sealed and attached to membrane 205 by adhesives, welding or mechanical fasteners. Gasket 107 seals interior portion 207 of inflatable dome 103 against wound area 203 and surrounding skin portion 105. In the preferred embodiments, gasket 107 is a ring-shaped flexible member made of a hypoallergenic polymer material such as MicroSkin available from Cymed.

In the preferred embodiments, upper gasket surface 107A of seal gasket 107 and lower dome seal surface 209 of dome peripheral portion 211 are releasable and re-sealable with respect to each other. In one preferred embodiment, the releasable and re-sealable feature of surfaces 107A and 209 are provided by a releasable and re-sealable contact adhesive 213 fixed to surface 107A. Lower dome seal surface 209 is a smooth seal surface to which adhesive 213 releasably seals surface 107A. Alternatively, adhesive 213 is fixed to lower dome seal surface 209 and adhesive 213 is releasable and re-sealable to surface 107A. Adhesive 213 may be a pressure sensitive adhesive. The releasable (non-adhesive) surface may be treated to promote release from the releasable adhesive.

A second adhesive 215 attaches seal gasket 107 to surrounding skin portion 105. Adhesive 213 is a controlled degradable adhesive. In the preferred embodiments, second adhesive 215 is an age-degradable, septic and hypoallergenic adhesive. For the purposes of this disclosure, and age-degradable adhesive is one in which the adhesive capability with the skin decreases with time, either from a direct time dependent process, or a process in which time not an direct, but rather a substantial indirect, factor in the adhesive degradation process. The preferred time periods of degradability are those typical for wound healing, i.e. 3–14 days.

The age-degradable feature may be provided by a hydrocolloid adhesive such as Duoderm, available from ConvaTec. Hydrocolloid-based adhesives maintain adhesion to the skin until moisture saturation of the hydrocolloid component (typically 3–12 days, depending on hydrocolloid content and skin, wound and environmental conditions). The moisture saturation is age or time dependent in that moisture provided to the hydrocolloid component from the wound portion, the surrounding portion, and atmospheric moisture is cumulative with time.

Utilization of an age-degradable adhesive permits secure fastening of seal gasket 107 to surrounding skin portion 105 for a substantial period of time and sufficient for normal use of the apparatus. Upon age degradation of the adhesive, removal of seal gasket 107 is simple and painless, and completed without damage to the surrounding skin portion. In the preferred embodiments, adhesive 215 is attached to lower surface 107B of seal gasket 107.

Restricted discharge of gasses 208 through vents 217 of membrane 205 maintains inflation of interior portion 207 and provides ventilation of gasses discharged from wound area 203. Vents 217 provide restriction of gas entrapped in interior portion 207, resulting in a positive pressure in portion 207. Positive pressure provides the dome shape of membrane 205. Vents 217 may comprise one or more apertures in membrane 205 such as holes, slots, or perforations. Outer layer 219, made of a fabric, mesh or perforated material such as a fine polymeric mesh material, prevents introduction of foreign material into vents 217 while allowing escape of gasses exiting the vents. Outer layer 219 may be bonded to membrane 205 by adhesives, welding or fasteners.

Figure 3:
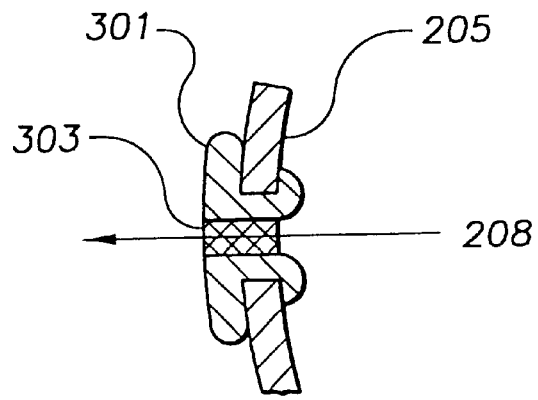
FIG. 3 is a detail cross section of a vent installed in the membrane of the inflatable dome of the apparatus.

FIG. 3 is a detail drawing of an alternative vent utilizing vent insert 301 attached to membrane 205. Vent 301 may be made of a polymeric, ceramic or metallic material. A contamination barrier or vent filter 303 allows venting of gasses 208 inside membrane 205 while preventing foreign material from entering vent 301. Filter 303 may be made of natural or synthetic fiber material, or sintered metal or ceramic materials.

Referring back to FIG. 2, an inner layer 221 of a sterile material such as sterile gauss may be bonded to the inner side of membrane 205. Inner layer 221 may be a natural or synthetic woven, non-woven or mesh material, or, other dressing materials known in the art. Inner layer 221 prevents membrane 205 from sticking to wound area 203. In the preferred embodiments, inner layer 221 is a breathable material, allowing covering of vents 217 and/or nozzle 111 and yet permitting flow of treatment gas into interior portion 207 and gasses out of interior portion 207. In other embodiments, cutouts or positioning of inner layer 221 prevents covering of vents 217 and/or nozzle 111.

In use, seal gasket 107 is attached to surrounding skin portion 105 surrounding wound area 203, utilizing an adhesive such as age-degradable adhesive 215. A skin preparation agent may be used to remove contaminates from the skin and provide a thin protective film before application of the age-degradable adhesive. Removal of a peel strip (not shown) exposes releasable adhesive 213 on upper gasket surface 107A. Releasable adhesive 213 bonds lower dome seal surface 209 of inflatable dome 103 to seal gasket 107. Alternatively, this may be a mechanical connection. The user removes peel strips (not shown) from electrode patches 117 and applies to surrounding skin portion 105A. Surrounding skin portion 105A is preferably upstream from a blood supply in relation to the wound so that the electrode patches will promote blood supply to wound area 203 upon energizing the patches.

Attachment of plugs 119 to supply hose 119 promotes correct use of the electrode patches since the physical attachment of the patches to the apparatus reminds the user to use and connect them. The placement of plugs 119 and the length of wire 121 promotes placement of the patches near the wound area where they are most effective. In alternative embodiments, additional electrode patches are attached to the apparatus.

Once dome portion 103 and electrode patches 117 are in place, the operator attaches oxygen hose 109 to a supply of oxygen, and stimulator power supply 118 to plugs 119. The operator then activates the oxygen supply and stimulator power supply 118.

Upon completion of the therapy, the operator may remove the dome portion by separating lower seal surface 209 of dome portion 103 from upper seal surface 107A. Tab 115 eases removal of dome portion 103. Re-sealable adhesive 213 allows removal and replacement of dome portion 103 without damage to the seal. In an alternative embodiment, a peel strip protects upper seal surface 107A when dome portion 103 is removed. Seal gasket 107 remains in place for several installations and removals of dome portion 103. Upon removal of dome portion 103, the wound may be cleaned or dressed or treated as directed.

Figure 4:
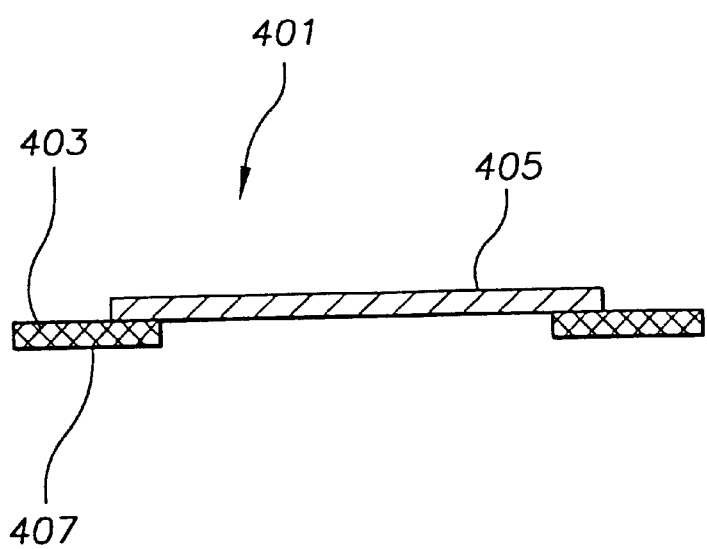
FIG. 4 is a cross section drawing of a dressing cover used in conjunction with the seal gasket of FIG. 1.

The wound may be covered by conventional dressings, or a dressing cover as shown in FIG. 4. Dressing cover 401 comprises a peripheral portion 403 of flexible material such as a polyolefin ring. A sterile dressing 405 covers the opening in peripheral portion 403. An adhesive bonds sterile dressing 405 to peripheral portion 403. Lower dressing seal surface 407 is sealable to upper seal gasket surface 107A.

In other embodiments, re-sealable adhesive 213 is fixed to dome lower seal surface 209 and lower dressing seal surface 407. The adhesive may be protected by a peel strip. In still other embodiments, oxygen nozzle 111 position provides physical stimulation of the wound by direct impingement of the gas on the wound area. Several nozzles placed to direct gas on the wound area provide additional stimulation In still other embodiments, inflatable dome 103 may have other shapes such as rectangular, oval or octagonal.

Accordingly the reader will see that the treatment apparatus for wounds disclosed and claimed provides improved apparatus and methods for treating wounds. The apparatus provides the following additional advantages:

Simultaneous application of a treatment gas such as oxygen to the wound and promotion of circulation afforded by the electrode patches provides an apparent synergetic effect to rapidly heal difficult wounds;

Use of a re-sealable adhesive on the seal gasket allows the inflatable dome to be removed and replaced frequently and easily, and with low cost;

Placement of the electrode patches on the device reminds the user to connect them and place them correctly; and Use of an age-degradable adhesive on the seal gasket allows simple and painless removal upon completion of use.

Although the description above contains many specifications, these should not be construed as limiting the scope of the invention but as merely providing illustrations of some of the presently preferred embodiments of this invention. For example, mechanical fasteners may attach the dome portion to the seal gasket, a re-sealable adhesive may be used on the lower dome seal surface and the device used without a seal gasket, or the inflatable dome may be made of a rigid material.

The simultaneous application of neuro-muscular stimulation and oxygen is believed to have a generally beneficial effect on the health of the treated skin, including the skin of humans and animals. Skin is an aerobic organism and the improved supply of oxygen provided by the present invention may have many beneficial effects. In one example, a treatment of oxygen and neruo-muscular electrical stimulation was applied periodically to the head of a bald man for between 2–3 hours daily. A standard RS Medical, Inc. Model RS-2 stimulator was used at a setting of Grade 6 to provide the electrical stimulation. In less than about 3 months, new hair began growing from the previously bald skin. It is believed that this effect resulted from the improved blood supply provided by the neuro-muscular stimulation in combination with the augmented oxygen made available to support the chemical reactions necessary to produce hair.

Figure 5:
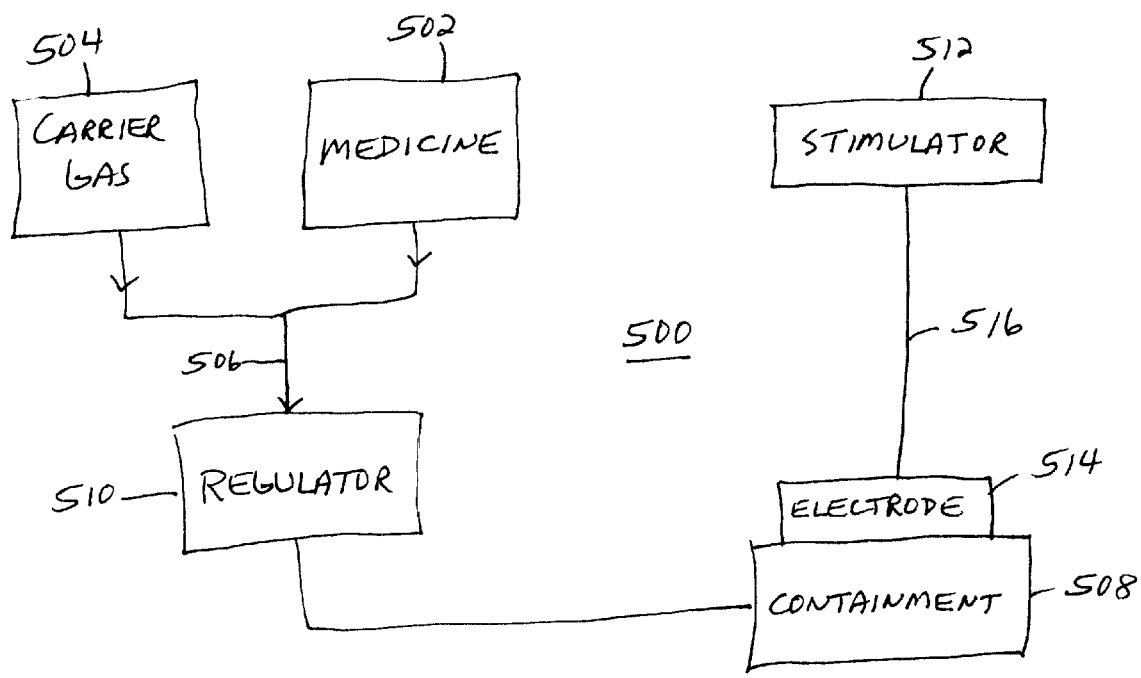
FIG. 5 is a block diagram of a skin treatment device for providing a treatment gas containing a medicine to the skin surface coincident with neuro-muscular stimulation.

It is also possible to deliver a medicine to the surface of the skin using the treatment apparatus 101 of FIG. 1. The increased blood and oxygen supply to the treated area of skin is believed to facilitate the absorption of such medicine through the skin surface. FIG. 5 is a schematic block diagram of a skin treatment device 500 used for the simultaneous application of a treatment gas and neruo-electrical stimulation to the skin. A supply of medicine 502 and a supply of a carrier gas 504 are interconnected to form a flow of treatment gas 506 for delivery to the skin via containment device 508. Containment device 508 may take the form of dome 103 of FIG. 1 or other such structure for directing the treatment gas to the skin surface. Containment device 508 may be removably attached to the skin or may be simply positioned proximate the wound and pressed into contact with the skin to provide a controlled flow of gas to a controlled area of the skin. Carrier gas 206 may be oxygen, air, an inert gas, nitrogen or other gas appropriate for a specific treatment. The treatment gas may be directed through a temperature regulator 510 prior to being delivered to the containment device 508 to achieve a predetermined temperature or regiment of temperatures as appropriate for the specific treatment. Regulator 510 may be used to increase or decrease the temperature of the treatment gas and may be any appropriate device or combination of heating/cooling devices known in the art. The flow of medicine may be constant or varied, and at times may be zero so that the flow of treatment gas 506 includes only the carrier gas 504.

A neuro-muscular stimulation device 512 is connected to at least one electrode 514 for the delivery of a current of electricity to the skin proximate the containment device 508. Electrodes 514 and/or the associated wires 516 may be physically attached to the containment device 508 for the convenience of the operator or may be provided separately. The stimulator 512 is preferably capable of providing a range of both AC and DC voltages and currents as may be preferred for a particular treatment routine.

Using device 500, medicine may be delivered at a controlled rate with a reduced chance of skin irritation when compared to known transdurmal patch devices. Furthermore, a controlled regiment of carrier gas, medicine, neuro-muscular stimulation, combination thereof, and temperature may be specified to achieve a desired effect. For an application intended to stimulate the growth of hair, the treatment apparatus 500 may be used to provide a hair growth medicine, such as Rogaine brand topical dermatological treatment provided by the Upjohn Company, along with oxygen in the treatment gas. A regiment of oxygenation and/or neuro-muscular stimulation applied with hair growth medicine and/or applied without hair growth medicine may be used. Other medicines, including for example vitamins, may be added in a particular hair growth regiment. For an application intended to retard the aging of skin and/or to reduce or eliminate wrinkles, a moisturizer, collagen and/or Vitamin E may be delivered along with oxygen and neuro-muscular stimulation. Other vitamins, minerals or compounds may be delivered for other applications, such as in the treatment of a specific nutrient deficiency.

For an application intended to heal a wound, medicines such as antibiotics and/or steroids may be included in the treatment gas. Unlike gels and lotions that are applied to the wound periodically, a wound healing medicine may be delivered at a continuous or predetermined variable rate with skin treatment device 500. Neuro-muscular stimulation provided by stimulator 512 and electrodes 514 will improve the distribution of the medicine throughout the area of treated skin and into the blood stream generally. In one regiment, the supply of oxygen is warmed to at least 103 degrees Fahrenheit. During a first time period, the oxygen is delivered to the skin surface along with a high dosage of antibiotic and neuro-muscular stimulation. The increase in circulation and improved oxygen levels in the skin cells will promote healing, and the high dosage of antibiotic will reduce the risk of infection. Thereafter, the delivery of a reduced dosage of antibiotic and neuro-muscular stimulation may be continued while the oxygen carrier gas is cooled to no warmer than 94 degrees Fahrenheit for a second period of time. Not only will the cool gas have a pleasant, pain relieving effect on the skin, it will also reduce the chance of infection. It is known that many undesirable types of bacteria thrive at temperatures between 96–102 degrees Fahrenheit, and accordingly, this temperature regiment will decrease the risk of infection.

Pain medicine may also be delivered with skin treatment device 500, either alone or together with other medications. One embodiment includes the delivery of pain medicine together with the antibiotic in the wound treatment regiment described above. The pain medicine may be a liquid or may be an anesthetic gas. The anesthetic gas may be used alone, as a carrier gas, or may be mixed with one or more other carrier gasses. In one regiment, pain-relieving medicine may be applied coincident with neuro-muscular stimulation in a carrier gas, such as oxygen or air, to at least partially interrupt the nerve synapse activity associated with pain. When liquid oxygen is used to generate the carrier gas, its delivery temperature is generally cool due to the natural heat absorption of an evaporating liquid. Alternatively, the carrier gas may be cooled artificially in temperature regulator 510 to a desired temperature to provide a further soothing sensation to the skin.

In a further aspect of this invention, treatment apparatus 101 may be used to assist in determining the rate of healing of a wound. In particular, seal gasket 107 may serve as a fixed base upon which a measuring grid may be repeatedly positioned in the same measuring position for periodically measuring the dimensions of a wound over a period of time. It is known that accurate recording of the size of a wound is important for evaluating the effectiveness of the therapy being used on the wound. The prior art technique for sizing a wound involves placing a grid over the lens of a camera, taking a series of pictures of the wound over time, and using the interposed grid pattern to estimate the size of the wound over time. The size of the wound is estimated by counting the number of grid spaces through which the wound is visible in the picture. The accuracy of this process is very sensitive to the distance of the camera lens/grid from the wound when each picture is taken. If the camera is moved away from the wound, the estimated wound size will be inaccurately small. Conversely, if the camera is moved closer to the wound, the estimated wound size will be inaccurately large. To keep the camera/grid a fixed distance from the wound, it is known to use a string attached to the camera to set the position of the camera for each picture. Not only is the accuracy of such a process less than desired, it also give rise to the possibility of the wound site being contaminated by touching the string.

Figure 6:
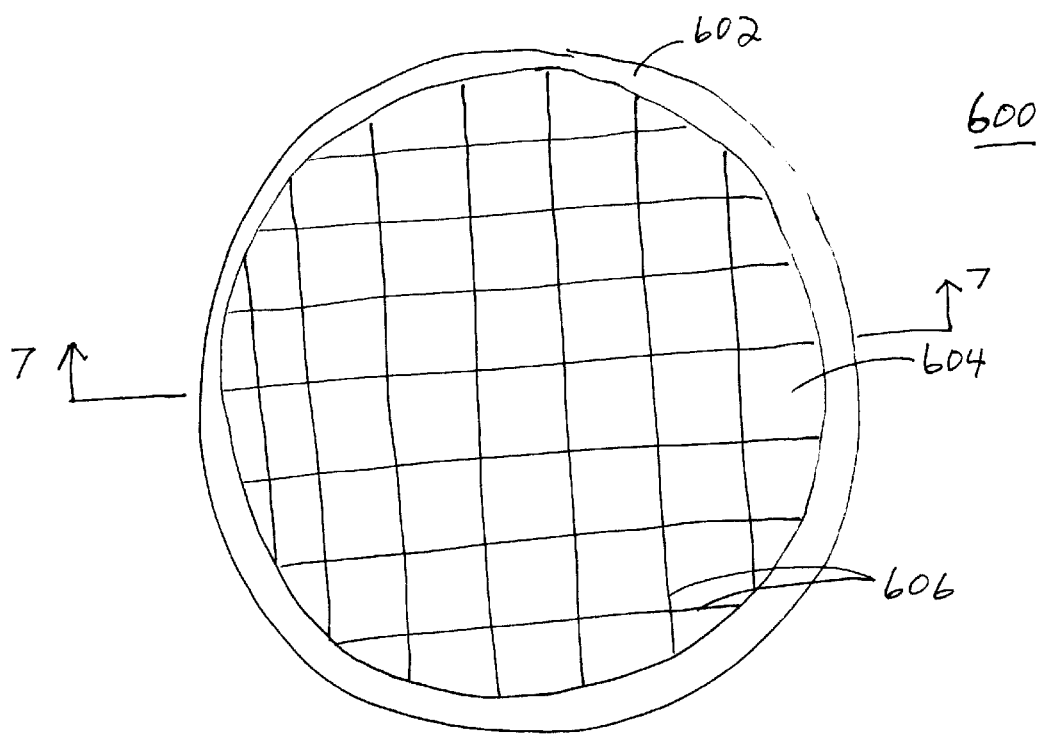
FIG. 6 is a top view of a wound measuring device that may be used with the apparatus of FIG. 1.
Figure 7:
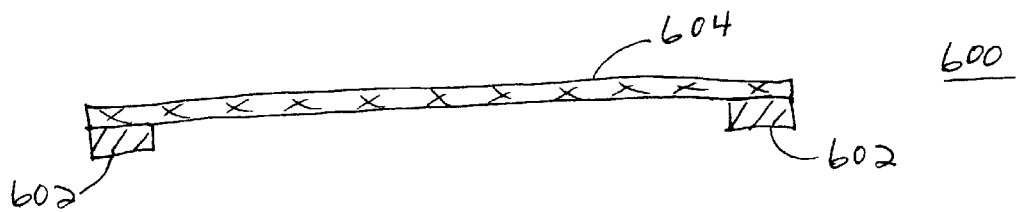
FIG. 7 is a side sectional view of the wound measuring device of FIG. 6.

A wound measuring device adapted for use with treatment apparatus 101 is illustrated in FIGS. 6 and 7. Wound measuring device 600 includes a frame portion 602 and a window portion 604. Frame portion 602 is may be round, rectangular or other desired shape for fitting around a wound or onto a particular portion of a body. Window portion 604 is made of a translucent or preferably transparent material such as a polymeric sheet or film such as polyolefin film. Printed on or otherwise disposed on or in the window portion 604 is a patterns of lines defining a grid pattern 606. Grid 606 may be opaque or of sufficient color density so that it is visible in contrast to the underlying skin when measuring device 600 is disposed over a wound. Grid 606 may take any shape or size as appropriate, and in one embodiment is a ¼ inch square pattern defining a plurality of transparent areas each having an area of approximately 0.0625 square inches. Preferably, frame portion 602 is sized or otherwise deigned to align precisely and repeatedly over the seal gasket 107 of treatment apparatus 101. In such a measurement position, grid 606 is disposed a fixed distance from the underlying skin and wound. The thickness of a seal gasket 107 may be, for example, from 0.1 inch to 0.5 inch, thus placing the grid very near to, but not touching the underlying wound. Because the grid 606 is positioned a fixed, small distance from the wound each time it is applied for a picture, the accuracy of the measurement of the size of the wound over a period of time becomes relatively insensitive to the distance of the camera lens from the grid/wound. The treatment gas containment portion 103 and the wound measuring device 600 are alternately attached to the seal gasket 107 in order to alternately treat the wound with a treatment gas and to measure the wound. Frame portion 602 may be made from a flexible material such as plastic in order to bend over curved portions of the skin. Frame portion 602 should also have sufficient rigidity to support window portion 604 taunt so as to maintain the grid pattern 606 in its predetermined shape. In one embodiment, a bottom surface 608 of the frame portion 602 and a top surface 107A of the seal gasket 107 may be formed with mating loop and hook type re-sealable fastening material. In an alternative embodiment, measuring device 600 may be used independent of treatment apparatus 101 by simply placing the frame portion 602 against the skin surrounding a wound when no seal gasket 107 is applied to the skin. In this embodiment, the thickness of frame portion 602 will determine the distance of the grid 606 from the skin/wound. With this embodiment, the position of the grid is not held constant in the plane of the skin from picture to picture. However, even in this embodiment, the distance between the wound and the grid 606 is held constant, thereby providing an improved method and apparatus for measuring a wound using photography when compared to the prior art technique.

Figure 8:
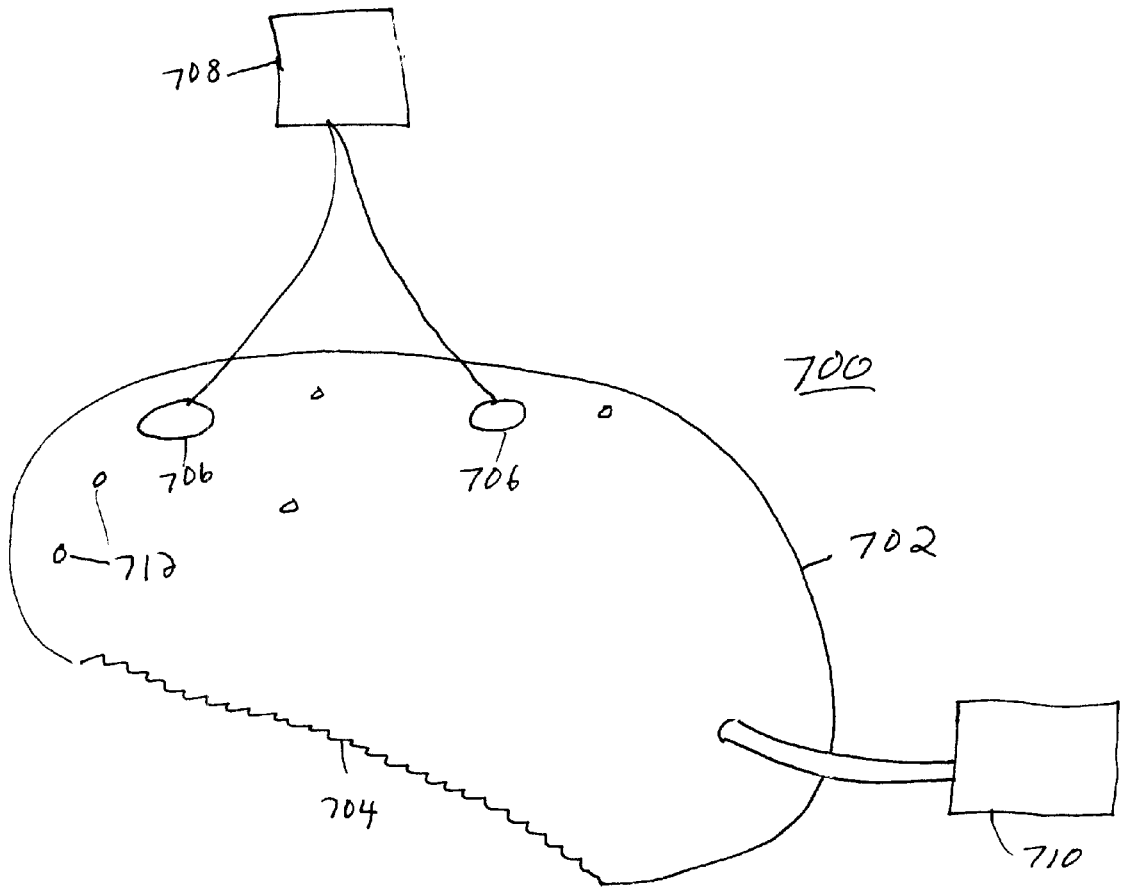
FIG. 8 is a device for applying treatment gas and neuro-muscular stimulation to the scalp.

FIG. 8 illustrates a device 700 for stimulating the growth of hair on a portion of skin on the head of a patient where hair growth is desired. The device 700 includes a gas containment cap portion 702 adapted for placement on the head of a patient. The containment 702 may be formed of plastic or other appropriate material and may have an elastic band 704 around an opening through which the patient's head is placed. One or more electrodes 706 are attached to the containment 702 in position to make contact with the scalp when the containment 702 is worn as a cap. The electrodes 706 are attached to a neuromuscular stimulation device 708 for applying an electrical current to the scalp. A supply of oxygen or other treatment gas 710 is connected to the containment, with the gas being directed over the scalp and out of the containment 702 through one or more vent openings 712. The treatment gas may include a medicine as described above. In this manner, both the treatment gas and electrical current may be applied simultaneously or in a predetermined pattern to the scalp in order to stimulate the growth of hair.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. A method for treating a wound, the method comprising:
   providing a flow of oxygen to a wound;
   applying an electrical current to a skin portion proximate the wound during the step of providing a flow of oxygen; and
   providing a flow of a medicine with the flow of oxygen.

2. The method of claim 1, further comprising:
   positioning a treatment gas applicator proximate the wound;
   placing at least one electrode in contact with the skin portion proximate the wound;
   providing the flow of oxygen to the treatment gas applicator while providing electrical current to the at least one electrode.

3. The method of claim 1, further comprising providing a flow of an antibiotic with the flow of oxygen.

4. The method of claim 1, further comprising providing a flow of a pain relief medicine with the flow of oxygen.

5. The method of claim 1, further comprising:
   providing the flow of oxygen at a temperature of at least 103 degrees Fahrenheit during a first time period; and
   providing the flow of oxygen at a temperature of no more than 94 degrees Fahrenheit during a second time period.

6. The method of claim 1, further comprising controlling temperature of the flow of oxygen to the wound to a predetermined temperature regiment.

7. The method of claim 1, further comprising controlling temperature of the flow of oxygen to the wound to a first temperature during a first time period and controlling temperature of the flow of oxygen to the wound to a second temperature cooler than the first temperature during a second time period.

8. A method of treating skin, the method comprising:
   providing a flow of a treatment gas to a skin surface;
   applying an electrical current to the skin surface during the step of providing a flow of treatment gas; and
   providing a medicine in the flow of treatment gas.

9. The method of claim 8, further comprising providing a vitamin in the flow of treatment gas.

10. The method of claim 8, further comprising providing oxygen as the treatment gas.

11. The method of claim 8, further comprising providing a flow of a pain medication with the flow of treatment gas.

12. The method of claim 8, further comprising providing a flow of a steroid with the flow of treatment gas.

13. The method of claim 8, further comprising providing a flow of an antibiotic with the flow of treatment gas.

14. The method of claim 8, further comprising providing a flow of a topical dermatological treatment with the flow of treatment gas.

15. The method of claim 8, further comprising providing a flow of a hair growth medicine with the flow of treatment gas.

16. The method of claim 8, further comprising controlling temperature of the flow of treatment gas to the skin surface to a predetermined temperature regiment.

17. The method of claim 8, further comprising controlling temperature of the flow of treatment gas to the skin surface to a first temperature during a first time period and controlling temperature of the flow of treatment gas to the skin surface to a second temperature cooler than the first temperature during a second time period.

18. A method of stimulating the growth of hair on skin, the method comprising:
   providing a flow of oxygen to a skin surface;
   applying an electrical current to the skin surface during the step of providing a flow of oxygen;
   periodically repeating the steps of providing a flow of oxygen to the skin surface and applying an electrical current to the skin surface during the step of providing a flow of oxygen; and
   providing a flow of hair growth medicine with the flow of oxygen.

19. The method of claim 18, further comprising:
   providing a gas applicator adapted to be worn around the head of a patient, the gas applicator comprising a gas containment portion and at least one electrode.

20. A method of stimulating the growth of hair on skin, the method comprising simultaneously applying neuromuscular stimulation and a flow of a treatment gas comprising oxygen and a hair growth medicine to a skin surface.

* * * * *